United States Patent [19]

Knifton

[11] Patent Number: 5,214,182
[45] Date of Patent: May 25, 1993

[54] PROCESS FOR COGENERATION OF ETHYLENE GLYCOL AND DIMETHYL CARBONATE

[75] Inventor: John F. Knifton, Austin, Tex.

[73] Assignee: Texaco Chemical Company, White Plains, N.Y.

[21] Appl. No.: 726,715

[22] Filed: Jul. 1, 1991

Related U.S. Application Data

[63] Continuation of Ser. No. 419,010, Oct. 10, 1989, abandoned, which is a continuation of Ser. No. 2,464, Jan. 12, 1987, abandoned.

[51] Int. Cl.$^5$ .............................................. C07C 69/96
[52] U.S. Cl. .................................. 558/277; 568/853; 568/858
[58] Field of Search ....................... 558/277; 568/858

[56] References Cited

U.S. PATENT DOCUMENTS

| | | | |
|---|---|---|---|
| 3,803,201 | 4/1974 | Gilpin et al. | 558/277 |
| 4,062,884 | 12/1977 | Romano et al. | 558/277 |
| 4,181,676 | 1/1980 | Buysch et al. | 558/277 |
| 4,307,032 | 12/1981 | Krimm et al. | 558/277 |
| 4,349,486 | 9/1982 | Brunelle et al. | 558/277 |
| 4,559,180 | 12/1985 | Green | 558/277 |

FOREIGN PATENT DOCUMENTS 2615665 10/1976 Fed. Rep. of Germany ...... 558/277

*Primary Examiner*—Jose G. Dees
*Assistant Examiner*—B. Frazier
*Attorney, Agent, or Firm*—James L. Bailey; Kenneth R. Priem; Cynthia L. Kendrick

[57] ABSTRACT

A process is disclosed for the cogeneration of ethylene glycol and dimethyl carbonate by reacting methanol and ethylene carbonate in the presence of a heterogeneous, phosphine-bound polymer catalyst. Dimethyl carbonate and ethylene glycol are generated in greater than 98% selectivity.

1 Claim, No Drawings

PROCESS FOR COGENERATION OF ETHYLENE GLYCOL AND DIMETHYL CARBONATE

This is a continuation of U.S. Ser. No. 07/419,010, now abandoned, which is a continuation of U.S. Ser. No. 07/002,464, now abandoned.

This invention concerns a process for cogeneration of ethylene glycol and dimethyl carbonate by the transesterification reaction of ethylene carbonate and methanol using a polymer bound tertiary phosphine on an organic copolymer. Ethylene glycol and dimethyl carbonate are generated in high yield under mild conditions using the phosphine bound polymer.

This case is related to applicant's U.S. application Ser. Nos. 06/815,954, now U.S. Pat. No. 4,691,041; 06,891,093, now U.S. Pat. No. 4,661,609; 06/924,072, now abandoned; and to U.S. application Ser. No. 07/002,463, now U.S. Pat. No. 4,734,518.

BACKGROUND OF THE INVENTION

Generally the prior art reports that the transesterification of aliphatic hydroxy compounds with carbonic acid, aliphatic diesters and aromatic diesters occurs readily in the presence of a basic catalyst and is a convenient method of synthesis of higher carbonates.

Several references deal with the transesterification of glycol carbonates using an aliphatic alcohol. Most demonstrate the use of methanol and ethylene carbonate.

U.S. Pat. No. 4,307,032 discloses a process for the preparation of a dialkyl carbonate by contacting a glycol carbonate of a 1,2-diol containing 2 to 4 carbon atoms with a selected alcohol to form the corresponding carbonate of said alcohol at a temperature of between 50° and 250° C., in the presence of an improved catalyst which is a thallium compound, allowing the reaction to take place under milder conditions. Thallium is however expensive and very toxic.

In another process disclosed in U.S. Pat. No. 4,181,676 there is taught a method for preparation of dialkyl carbonate by contacting a glycol carbonate of a 1,2-diol having 2 to 4 carbon atoms with a selected group of alcohols at an elevated temperature in the presence of an alkali metal or alkali metal compound wherein the improvement comprises employing less than 0.01 percent by weight of alkali metal or alkali metal compound based on the weight of the reaction mixture.

It is known that alkyl carbonates of the type ROCOOR can be obtained from alcohols and cyclic carbonates corresponding to the above formula through a transesterification reaction in the presence of alkali alcoholates or hydrates; however, moderate amounts of inorganic compounds are produced by these reactions and must be removed by methods which may unfavorably affect the general economy of the process.

In U.S. Pat. No. 4,062,884 this efficiency problem was addressed and it was found that dialkyl carbonates can be prepared by reacting alcohols with cyclic carbonates in the presence of organic bases, which makes it unnecessary to remove inorganic compounds and allows the catalyst to be totally recovered by means of simple distillation. The preferred organic base is a tertiary aliphatic amine.

U.S. Pat. No. 4,349,486 teaches a monocarbonate transesterification process comprising contacting a beta-fluoroaliphatic carbonate and a compound selected from the class of monohydroxy aliphatic alcohols, monohydroxy phenols and ortho-positioned dihydroxy aromatic compounds in the presence of a base. This invention claims to greatly reduce undesirable side reactions and only small amounts of carbonic acid-aliphatic-aromatic mixed diester are associated with the isolated aromatic monocarbonate reaction.

The Gilpin and Emmons Patent, U.S. Pat. No. 3,803,201, discusses problems associated with the separation of the methanol, dimethyl carbonate azeotrope and teaches a solution wherein dimethyl carbonate is isolated from the azeotrope by a combination of low temperature crystallization and fractional distillation.

In another article in the J. Org. Chem. 49(b) 1122-1125 (1984) Cella and Bacon discuss the results of their work. Among other things, they found that the alkylation of alkali metal bicarbonate and carbonate salts with alkyl halides in dipolar aprotic solvents and phase-transfer catalysts produces alkyl carbonates in good yields. The major limitation of this method is the failure of activated aryl halides or electronegatively substituted alkyl halides to produce carbonates due to the facility with which the intermediate alkoxy carbonate salts decompose.

In Japanese Patent No. 4,028,542-B there is disclosed a method for preparation of dialkyl carbonates from cyclic carbonates by reacting an alcohol with a cyclic carbonate having the formula:

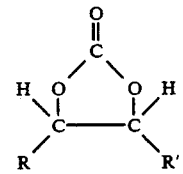

where R and R' are H or alkyl, in the presence of an organic base catalyst such as a tertiary amine. The advantage is that organic products do not have to be removed and catalysts can be recovered by distillation.

Disadvantages of the methods discussed above include in many cases the fact that it is necessary to use a large amount of methanol feedstock relative to the amount of dimethyl carbonate produced. Side reactions to unwanted products and efficient separation of the desired products can also present problems. Also, in many cases, alkali metal halides are coproduced and these halides present disposal problems.

In applicant's related application, U.S. Ser. No. 06/815,954, now U.S. Pat. No. 4,691,041, there is disclosed a new route to dimethyl carbonate using a heterogeneous catalyst comprising specified classes of ion exchange resins. This improved method requires fewer moles of methanol per mole of dimethyl carbonate.

Related Ser. No. 06/891,093, now U.S. Pat. No. 4,661,609, produces good yields of dimethyl carbonate and ethylene glycol simultaneously in the presence of a homogeneous catalyst of zirconium, titanium or tin.

Applicant's Ser. No. 06/924,072, now abandoned, coproduces high yields of dimethyl carbonate and ethylene glycol under mild conditions, using perfluorinated ion exchange resins.

It would be a substantial advance in the art to devise an efficient process for co-producing dimethyl carbonate and ethylene glycol in improved yields using mild conditions. It would also be desirable if the catalyst system minimized side reactions and allowed for efficient separation of the product. In the instant process the concentrations of ethylene glycol (EG) and dimethyl carbonate (DMC) in the crude liquid products are as high as 13.5 wt % and 21.4 wt % respectively and the selectivity to dimethyl carbonate and ethylene glycol is up to greater than 98%. The concentrations of DMC and EG in the crude liquid product are close to equilibrium. The dimethyl carbonate produced by this novel process can be used as a gasoline extender.

SUMMARY OF THE INVENTION

This invention concerns a process for the cogeneration of ethylene glycol and dimethyl carbonate from ethylene carbonate and methanol by reacting ethylene carbonate and methanol in the presence of a catalyst comprising a polymer bound tertiary phosphine on a styrene-divinylbenzene copolymer at a temperature of from 20° C. to 200° C. and an operative pressure of zero to 5000 psig, until the desired products are formed.

A particular advantage of this system over the prior art is that ethylene glycol and dimethyl carbonate are generated in high yields under mild conditions using the phosphine polymer. These selectivities are illustrated in accompanying Examples 1-12 using a tertiary phosphine, polymer-bound, catalyst.

DETAILED DESCRIPTION OF THE INVENTION

In the narrower and more preferred practice of this invention dimethyl carbonate and ethylene glycol are prepared simultaneously by a transesterification process which comprises reacting ethylene carbonate and methanol in the presence of a polymer bound tertiary phosphine on a styrene-divinylbenzene copolymer, at a temperature of between 50° C. and 150° C. and a pressure of at least 50 psig, until the desired products are formed.

The reaction can be represented by the following equation:

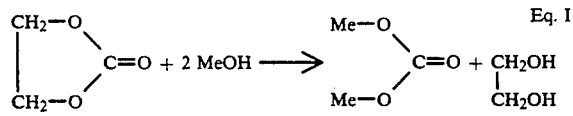

Eq. I

Starting materials employed in the process comprise an aliphatic alcohol and an aliphatic carbonate. Alcohols which work in the process of this invention include the monohydric alcohols containing one to 14 carbon atoms, including methanol, ethanol, isopropanol and isobutanol. Methanol is the preferred alcohol. Alkylene carbonates which will work in the process of this invention include the carbonate derivatives of 1,2-diols containing two to 10 carbon atoms per molecule, including ethylene carbonate, 1,2-propylene carbonate and 1,2-butanediol carbonate. Ethylene carbonate is the preferred alkylene carbonate feedstock for this process. The preferred starting materials are illustrated in accompanying Examples 1-12. Recovery of the desired ethylene glycol and dimethyl carbonate can generally be carried out by distillation and crystallization.

More specifically, methanol and ethylene carbonate are pumped into a tubular reactor upflow at a flow rate of 0.1 to 100 liquid hourly space velocity (LHSV). The reactor temperature is held at between 20° and 200° C. and a back pressure of zero to 5000 psi is maintained throughout the experiment.

The polymer bound catalyst systems suitable for the practice of this invention generally comprise solid polymer-bound phosphine systems. The tertiary phosphine polymer-bound catalysts useful in this invention are solid resin systems with alkyl and aryl phosphines covalently bonded to organic polymers.

Examples of suitable alkyl and aryl phosphines include triphenylphosphine, tri-n-butylphosphine, tri-p-tolylphosphine, tri-n-hexylphosphine, tri-c-hexylphosphine, diphenylmethylphosphine, phenyldimethylphosphine and tribenzylphosphine as well as diphenylphosphine, diethylphosphine and halogen-substituted alkyl and aryl phosphines such as diphenylchlorophosphine.

The solid polymer component of this catalyst system may comprise any organic polymer unit, but preferably it is a solid, high MW, polymer containing an aromatic or N-heterocyclic ring system, such as the styrene, methylstyrene or vinylpyridine polymers. Resin systems that work well are the styrene-divinylbenzene copolymers. These macroporous copolymers may comprise 0.1 to 50% cross-linkages.

The tertiary phosphine polymer bound catalysts of this invention may be employed as solid resin systems in the form of powders. Also effective may be pellets, extrudates and granules. A particularly effective catalyst for the cosynthesis of dimethyl carbonate and ethylene glycol is a polymer-bound triphenylphosphine on a styrene-divinyl benzene polymer (2% to 20% crosslinked). This form of catalyst is illustrated in the accompanying examples.

During the cosynthesis of ethylene glycol and dimethyl carbonate by the reaction of ethylene carbonate with methanol, a large excess of methanol is usually required according to processes in the art. Usually the initial molar ratio of methanol to ethylene carbonate is in the range of 5 or greater, and preferably at least 10. This preferred ratio range is illustrated by U.S. Pat. No. 3,803,201 (1974). In the practice of the instant invention, by contrast, the initial weight ratio of ethylene carbonate to methanol is preferable in the range of from 1:1 to 1:5 and most preferably 2 to 3. Such a range of weight ratios is illustrated by the accompanying examples.

Potential advantages to operating at this ethylene carbonate-to-methanol weight ratio include:

a) More efficient transesterification.

b) Lower levels of methanol required to be recycled after the transesterification step.

Ethylene glycol-dimethyl carbonate synthesis using the heterogeneous polymer-bound catalyst described SUPRA can be conducted at reaction temperatures in the range from 20° to 200° C. The preferred operating temperature range is 50°-150° C.

The reaction can be conducted under atmospheric pressure. A pressure reactor is nevertheless required in the case of low-boiling point components if the reaction is to be carried out in the upper temperature range and in the liquid phase. The pressure is not critical. In general the reaction is allowed to proceed under the autogenous pressure of the reactants. However, the reaction can also be carried out under elevated pressure, for example, under an inert atmosphere. A pressure of zero to 5000 psig is appropriate here. An operating pressure of greater than 50 psig is suitable and the preferred pressure is in the range of 50 to 150 psi.

The residence time for the ethylene carbonate and methanol reactants in the tubular reactor may vary over a wide range according to the temperature of reaction, the molar ratios of carbonate/alcohol feedstocks, etc. Using the heterogeneous catalysts of this invention, the necessary residence time in the reactor may range from 0.01 hours to 10 hours, although it may be extended beyond 10 hours without danger of additional by-products being formed. The preferred residence time is in the range of 0.1 to 5 hours.

The desired products of this process according to the invention are ethylene glycol and dimethyl carbonate. By-products are primarily ethylene glycol monoalkyl ethers, such as glycol monomethyl ether(EGMME); others, including diethylene glycol, 1,1-dimethoxyethane, 1,2-dimethoxyethane, methyl 1,3-dioxolane, and dimethyl ether may be formed in trace quantities.

Products have been identified in this work by gas chromatography (gc), NMR, IR and gc-IR or a combination of these techniques. All liquid product analyses have, for the most part, been by gc; all temperatures are in degrees centigrade and all pressures in pounds per square inch gauge.

The following examples illustrate the novel process of this invention. The examples are only for illustrating the invention and are not considered to be limiting.

EXAMPLE 1

Example I illustrates the cosynthesis of ethylene glycol and dimethyl carbonate using, as the heterogeneous catalyst, a phosphine-bound polymer.

The synthesis was conducted in a 50-cc capacity tubular reactor, constructed of 316 stainless steel, operated upflow and mounted in a furnace controllable to +/−1.0° C. and fitted with pumps allowing flow control of ±1/cc/hr. The reactor was also fitted with a pressure regulating device and equipment for monitoring temperature, pressure and flow rate.

The reactor was charged at the beginning of the experiment with 25 g of polymer-bound triphenylphosphine on styrene-divinylbenzene copolymer (2% cross-linked 3.1 mmole Ph$_3$P/g polymer, 20–60 mesh). Glass wool plugs were placed at the top and bottom of the reactor to ensure the powder would remain in the middle portion.

The catalyst bed was first conditioned at 80° C. by washing with methanol (25 cc/hr) for 24 hours. A solution of methanol (1185 g, 37.0 mole) plus ethylene carbonate (815 g, 9.3 mole) was then pumped through the catalyst bed at 25 cc/hr, while the reactor was held at 125° C. at a total pressure of 100 psig. Samples of the product liquid were taken periodically and material after several hours running time typically showed the following composition:

21.4 wt % dimethyl carbonate (DMC)
13.5 wt % ethylene glycol (EG)
26.8 wt % ethylene carbonate (EC)
36.9 wt % methanol (MeOH)

Estimated selectivity to dimethyl carbonate basis ethylene carbonate converted = >98%.

It may be noted that in this example the concentrations of dimethyl carbonate and ethylene glycol in the crude liquid product are close to equilibrium.

EXAMPLES 2–3

Ethylene glycol and dimethyl carbonate were prepared from ethylene carbonate and methanol using the same equipment, procedures, phosphine-bound polymer catalyst and feed composition as in Example 1 but at two different reaction temperatures.

Results are shown in Table I:

TABLE I

| Example | Operating Temp. °C. | Product Liquid Comp. WT % | | | |
|---|---|---|---|---|---|
| | | DMC | EG | EC | MeOH |
| 2 | 80 | 6.4 | 3.9 | 33.0 | 55.7 |
| 3 | 100 | 16.9 | 10.9 | 31.0 | 40.3 |

EXAMPLES 4–7

Examples 4–7 were conducted in the same 50-cc capacity tubular reactor of Example 1 using the same operating procedures.

The reactor was charged with 25 cc of polymer-bound triphenylphosphine on styrene-divinylbenzene copolymer that had been pretreated with methanol and MeOH/EC feed. A solution of methanol plus ethylene carbonate (1:1 wt. ratio) was then pumped through the catalyst bed at various pump rates, while the reactor was held at temperatures of 125° C. and 140° C. Samples of the product liquid were taken periodically and material after several hours running time typically showed the compositions listed in Table II:

TABLE II

| Example | Operating Temp. °C. | Feed Rate (cc/hr) | Product Liquid Comp. Wt % | | | |
|---|---|---|---|---|---|---|
| | | | DMC | EG | EC | MeOH |
| 4 | 125 | 12 | 19.2 | 13.2 | 37.6 | 28.8 |
| 5 | 125 | 50 | 15.9 | 6.9 | 45.9 | 30.5 |
| 6 | 125 | 200 | 14.9 | 6.2 | 38.6 | 39.5 |
| 7 | 140 | 25 | 18.2 | 7.7 | 29.4 | 43.5 |

EXAMPLES 8–12

In Examples 8 through 12, the procedures used were the same as those of Examples 1–8, but the catalyst was 15 g of polymer-bound triphenylphosphine on styrene-divinylbenzene copolymer (20% cross-linked). Both temperature and flow rate were varied. Results are shown in Table III.

It may be seen that this phosphine on styrene-divinylbenzene copolymer is also effective for dimethyl carbonate-ethylene glycol cosynthesis. With this catalyst, near equilibrium concentrations of DMC (19.4 wt %) and EG (11.9 wt %) may be obtained in the crude liquid product at 140° C. and a liquid flow rate of 12 cc/hr. (Example II).

TABLE III

| Ex. | Catalyst | Flow rate (cc/hr.) | Temp. (°C.) | Sample | Product Liquid Comp. Wt % | | | |
|---|---|---|---|---|---|---|---|---|
| | | | | | DMC | EG | EC | MeOH |
| 8 | Polymer-Bound Triphenylphosphine on styrene-divinylbenzene Polymer (20% cross-linked)[a] | 25 | 100 | −13 | 3.8 | 2.3 | 34.8 | 58.3 |
| 9 | | 25 | 120 | −6 | 5.8 | 3.6 | 31.7 | 58.2 |
| 10 | | 12 | 120 | −11 | 12.9 | 7.8 | 25.6 | 53.1 |
| 11 | | 12 | 140 | −20 | 19.4 | 11.9 | 19.9 | 48.2 |

TABLE III-continued

| Ex. | Catalyst | Flow rate (cc/hr.) | Temp. (°C.) | Sample | DMC | EG | EC | MeOH |
|---|---|---|---|---|---|---|---|---|
| 12 | | 200[b] | 140 | −37 | 2.9 | 2.4 | 39.8 | 51.8 |

[a]Fresh catalyst sample, used 15 g in reactor
[b]New Feed F-1

I claim:

1. A process for the cosynthesis of ethylene glycol and dimethyl carbonate up to 98% selectivity which consists of reacting ethylene carbonate and methanol in a weight ratio in the range of 1:1 to 1:5 in the presence of a heterogeneous catalyst consisting of triphenylphosphine bound to a styrene-divinylbenzene copolymer having 2 to 20% cross-linkages at a temperature of 50° C. to 150° C., wherein the operating pressure is between 0 and 5000 psig until the desired products are obtained.

* * * * *